(12) United States Patent
Taylor et al.

(10) Patent No.: US 10,230,041 B2
(45) Date of Patent: Mar. 12, 2019

(54) METHODS OF PLATING OR COATING ULTRASOUND TRANSDUCERS

(71) Applicant: ReCor Medical, Inc., Palo Alto, CA (US)

(72) Inventors: Kevin Taylor, San Mateo, CA (US); Paul Chandler, Santa Cruz, CA (US)

(73) Assignee: ReCor Medical, Inc., Palo Alto, CA (US)

( * ) Notice: Subject to any disclaimer, the term of this patent is extended or adjusted under 35 U.S.C. 154(b) by 721 days.

(21) Appl. No.: 14/210,007

(22) Filed: Mar. 13, 2014

(65) Prior Publication Data

US 2014/0272110 A1 Sep. 18, 2014

Related U.S. Application Data

(60) Provisional application No. 61/784,164, filed on Mar. 14, 2013.

(51) Int. Cl.
*H01L 41/297* (2013.01)
*C23C 18/16* (2006.01)
(Continued)

(52) U.S. Cl.
CPC .......... *H01L 41/297* (2013.01); *A61B 8/4483* (2013.01); *B06B 1/0662* (2013.01);
(Continued)

(58) Field of Classification Search
CPC ........ H01L 41/29; H01L 41/297; H01L 41/00
USPC ...... 427/304, 97.9, 99.5, 437, 443.1, 9, 105, 427/230, 476, 100; 310/334, 369, 322, 310/355, 345, 642; 340/363; 29/594;
(Continued)

(56) References Cited

U.S. PATENT DOCUMENTS 3,938,502 A 2/1976 Bom
4,841,977 A 6/1989 Griffith et al.
(Continued)

FOREIGN PATENT DOCUMENTS

DE 20 2005 022 060 U1 11/2012
EP 0 623 360 B1 11/1994
(Continued)

OTHER PUBLICATIONS http://www.dictionary.com/browse/degrease. No Date.*
(Continued)

*Primary Examiner* — Tabassom Tadayyon Eslami
(74) *Attorney, Agent, or Firm* — Foley & Lardner LLP; Christopher C. Bolten; Nicola A. Pisano

(57) ABSTRACT

According to some embodiments, a method of depositing at least one electrode on a base member of an ultrasound transducer comprises at least partially etching a surface of the base member using a first etching agent, catalyzing the surface of the base member using a first catalyst, plating copper on the surface of the base member using an electroless plating process, inspecting the copper plated on the surface of the base member, at least partially etching a surface of the copper-plated surface using a second etching agent, catalyzing the copper-plated surface using a second catalyst, plating nickel on the copper-plated surface using an electroless plating process and depositing at least one layer of gold on the nickel-plated surface.

19 Claims, 1 Drawing Sheet

(51) Int. Cl.

| | | |
|---|---|---|
| *C23C 18/18* | (2006.01) | |
| *C23C 18/54* | (2006.01) | |
| *H01L 41/29* | (2013.01) | |
| *B06B 1/06* | (2006.01) | |
| *A61B 8/00* | (2006.01) | |
| *C23C 18/36* | (2006.01) | |
| *C23C 18/38* | (2006.01) | |

(52) U.S. Cl.
CPC ...... *C23C 18/1651* (2013.01); *C23C 18/1675* (2013.01); *C23C 18/1893* (2013.01); *C23C 18/54* (2013.01); *H01L 41/29* (2013.01); *C23C 18/36* (2013.01); *C23C 18/38* (2013.01)

(58) Field of Classification Search
USPC ...... 600/395, 437; 216/6, 16, 30, 31, 34, 74, 216/76, 80, 96, 97, 99, 103, 104, 106, 216/107, 108, 109
See application file for complete search history.

(56) References Cited

U.S. PATENT DOCUMENTS

| | | | |
|---|---|---|---|
| 5,295,992 | A | 3/1994 | Cameron |
| 5,295,995 | A | 3/1994 | Kleiman |
| 5,308,356 | A | 5/1994 | Blackshear et al. |
| 5,324,255 | A | 6/1994 | Passafaro et al. |
| 5,327,885 | A | 7/1994 | Griffith |
| 5,354,200 | A | 10/1994 | Klein et al. |
| 5,354,220 | A | 10/1994 | Ganguly et al. |
| 5,400,267 | A | 3/1995 | Denen et al. |
| 5,423,220 | A * | 6/1995 | Finsterwald ......... B06B 1/0622 310/322 |
| 5,456,259 | A | 10/1995 | Barlow et al. |
| 5,524,491 | A * | 6/1996 | Cavalloni ............ G10K 11/02 73/587 |
| 5,620,479 | A | 4/1997 | Diederich |
| 5,630,837 | A | 5/1997 | Crowley |
| 5,713,849 | A | 2/1998 | Bosma et al. |
| 5,769,812 | A | 6/1998 | Stevens et al. |
| 5,775,338 | A | 7/1998 | Hastings |
| 5,803,083 | A | 9/1998 | Buck et al. |
| 5,938,645 | A | 8/1999 | Gordon |
| 6,097,985 | A | 8/2000 | Kasevich et al. |
| 6,102,863 | A | 8/2000 | Pflugrath et al. |
| 6,117,101 | A | 9/2000 | Diederich et al. |
| 6,128,522 | A | 10/2000 | Acker et al. |
| 6,149,596 | A | 11/2000 | Bancroft |
| 6,190,377 | B1 | 2/2001 | Kuzdrall |
| 6,216,704 | B1 | 4/2001 | Ingle et al. |
| 6,277,077 | B1 | 8/2001 | Brisken et al. |
| 6,299,583 | B1 | 10/2001 | Eggers et al. |
| 6,355,030 | B1 | 3/2002 | Aldrich et al. |
| 6,475,146 | B1 | 11/2002 | Frelburger et al. |
| 6,492,762 | B1 | 12/2002 | Pant et al. |
| 6,517,534 | B1 | 2/2003 | McGovern et al. |
| 6,599,256 | B1 | 7/2003 | Acker et al. |
| 6,599,288 | B2 | 7/2003 | Maguire et al. |
| 6,607,502 | B1 | 8/2003 | Maguire et al. |
| 6,635,054 | B2 | 10/2003 | Fjield et al. |
| 6,645,202 | B1 | 11/2003 | Pless et al. |
| 6,712,767 | B2 | 3/2004 | Hossack et al. |
| 6,712,836 | B1 | 3/2004 | Berg et al. |
| 6,763,722 | B2 | 7/2004 | Fjield et al. |
| 6,793,635 | B2 | 9/2004 | Ryan et al. |
| 6,913,581 | B2 | 7/2005 | Corl et al. |
| 6,953,469 | B2 | 10/2005 | Ryan |
| 6,978,174 | B2 | 12/2005 | Gelfand et al. |
| 7,162,303 | B2 | 1/2007 | Levin et al. |
| 7,285,116 | B2 | 10/2007 | De La Rama et al. |
| 7,297,413 | B2 | 11/2007 | Mitsumori |
| 7,347,852 | B2 | 3/2008 | Hobbs et al. |
| 7,473,224 | B2 | 1/2009 | Makin |
| 7,540,846 | B2 | 6/2009 | Harhen et al. |
| 7,617,005 | B2 | 11/2009 | Demarais et al. |
| 7,620,451 | B2 | 11/2009 | Demarais et al. |
| 7,625,371 | B2 | 12/2009 | Morris et al. |
| 7,647,115 | B2 | 1/2010 | Levin et al. |
| 7,653,438 | B2 | 1/2010 | Deem et al. |
| 7,678,104 | B2 | 3/2010 | Keidar |
| 7,717,948 | B2 | 5/2010 | Demarais et al. |
| 7,756,583 | B2 | 7/2010 | Demarais et al. |
| 7,837,676 | B2 | 11/2010 | Sinelnikov et al. |
| 7,846,317 | B2 * | 12/2010 | Meltzer ................. C25D 3/562 174/250 |
| 7,873,417 | B2 | 1/2011 | Demarais et al. |
| 7,937,143 | B2 | 5/2011 | Demarais et al. |
| 8,131,371 | B2 | 3/2012 | Demarals et al. |
| 8,233,221 | B2 | 7/2012 | Suijver et al. |
| 8,251,986 | B2 | 8/2012 | Chornenky et al. |
| 8,287,472 | B2 | 10/2012 | Ostrovsky |
| 8,475,442 | B2 | 7/2013 | Hall et al. |
| 8,485,993 | B2 | 7/2013 | Orszulak et al. |
| 8,504,147 | B2 | 8/2013 | Deem et al. |
| D697,036 | S | 1/2014 | Kay et al. |
| 8,715,209 | B2 | 5/2014 | Gertner |
| 8,734,438 | B2 | 5/2014 | Behnke |
| D708,810 | S | 7/2014 | Lewis, Jr. |
| 8,808,345 | B2 | 8/2014 | Clark et al. |
| D712,352 | S | 9/2014 | George et al. |
| D712,353 | S | 9/2014 | George et al. |
| D712,833 | S | 9/2014 | George et al. |
| 8,974,445 | B2 | 3/2015 | Warnking et al. |
| 9,675,413 | B2 | 6/2017 | Deem et al. |
| 2001/0007940 | A1 | 7/2001 | Tu et al. |
| 2002/0002334 | A1 | 1/2002 | Okuno et al. |
| 2002/0002371 | A1 | 1/2002 | Acker et al. |
| 2002/0065512 | A1 | 5/2002 | Fjield et al. |
| 2002/0087156 | A1 | 7/2002 | Maguire et al. |
| 2002/0150693 | A1 * | 10/2002 | Kobayashi ............ C23C 18/163 427/443.1 |
| 2002/0151889 | A1 | 10/2002 | Swanson et al. |
| 2002/0156469 | A1 | 10/2002 | Yon et al. |
| 2002/0165535 | A1 | 11/2002 | Lesh et al. |
| 2002/0193781 | A1 | 12/2002 | Loeb |
| 2003/0060813 | A1 | 3/2003 | Loeb et al. |
| 2003/0138571 | A1 | 7/2003 | Kunishi et al. |
| 2003/0181963 | A1 | 9/2003 | Pellegrino et al. |
| 2003/0204138 | A1 | 10/2003 | Choi |
| 2003/0216721 | A1 | 11/2003 | Diederich et al. |
| 2003/0216792 | A1 | 11/2003 | Levin et al. |
| 2003/0216794 | A1 | 11/2003 | Becker et al. |
| 2003/0225331 | A1 | 12/2003 | Diederich et al. |
| 2003/0233099 | A1 | 12/2003 | Danaek et al. |
| 2004/0044286 | A1 | 3/2004 | Hossack et al. |
| 2004/0082859 | A1 | 4/2004 | Schaer |
| 2004/0167415 | A1 | 8/2004 | Gelfand et al. |
| 2004/0230116 | A1 | 11/2004 | Cowan et al. |
| 2004/0253450 | A1 * | 12/2004 | Seita ..................... C23C 18/30 428/411.1 |
| 2005/0009218 | A1 | 1/2005 | Kunihiro |
| 2005/0035901 | A1 | 2/2005 | Lyon |
| 2005/0215990 | A1 | 9/2005 | Govari |
| 2005/0234523 | A1 | 10/2005 | Levin et al. |
| 2005/0256518 | A1 | 11/2005 | Rama et al. |
| 2005/0288730 | A1 | 12/2005 | Deem et al. |
| 2006/0041277 | A1 | 2/2006 | Deem et al. |
| 2006/0058711 | A1 | 3/2006 | Harhen et al. |
| 2006/0064081 | A1 | 3/2006 | Rosinko |
| 2006/0088705 | A1 | 4/2006 | Mitsumori |
| 2006/0100514 | A1 | 5/2006 | Lopath |
| 2006/0121200 | A1 * | 6/2006 | Halpert ................. C04B 41/009 427/305 |
| 2006/0154072 | A1 | 7/2006 | Schlossman et al. |
| 2006/0155269 | A1 | 7/2006 | Warnking |
| 2006/0184072 | A1 | 8/2006 | Manna |
| 2006/0212076 | A1 | 9/2006 | Demarais et al. |
| 2006/0212078 | A1 | 9/2006 | Demarais et al. |
| 2006/0229594 | A1 | 10/2006 | Francischelli et al. |
| 2006/0241523 | A1 | 10/2006 | Sinelnikov et al. |
| 2006/0265014 | A1 | 11/2006 | Demarais et al. |
| 2006/0265015 | A1 | 11/2006 | Demarais et al. |
| 2006/0270976 | A1 | 11/2006 | Savage et al. |
| 2006/0276852 | A1 | 12/2006 | Demarais et al. |

(56) References Cited

U.S. PATENT DOCUMENTS

| | | |
|---|---|---|
| 2007/0124458 A1 | 5/2007 | Kumar |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0173899 A1 | 7/2007 | Levin et al. |
| 2007/0175359 A1 | 8/2007 | Hwang |
| 2007/0203547 A1 | 8/2007 | Costello et al. |
| 2007/0203549 A1 | 8/2007 | Demarais et al. |
| 2007/0255267 A1 | 11/2007 | Diederich et al. |
| 2007/0255342 A1 | 11/2007 | Laufer |
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Demarais et al. |
| 2007/0293762 A1* | 12/2007 | Sawada .................. A61B 8/12 600/459 |
| 2008/0052186 A1 | 2/2008 | Walker et al. |
| 2008/0151001 A1 | 6/2008 | Sudo et al. |
| 2008/0252172 A1* | 10/2008 | Yetter .................. B06B 1/0629 310/317 |
| 2008/0255449 A1 | 10/2008 | Warnking et al. |
| 2008/0255478 A1 | 10/2008 | Burdette |
| 2008/0255642 A1 | 10/2008 | Zarins et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118125 A1 | 5/2009 | Kobayashi et al. |
| 2009/0118725 A1 | 5/2009 | Auth et al. |
| 2009/0124964 A1 | 5/2009 | Leach et al. |
| 2009/0149753 A1 | 6/2009 | Govari et al. |
| 2009/0171202 A1 | 7/2009 | Kirkpatrick et al. |
| 2009/0189485 A1* | 7/2009 | Iyoki ..................... B82Y 35/00 310/317 |
| 2009/0204006 A1* | 8/2009 | Wakabayashi ........... A61B 8/12 600/463 |
| 2009/0221939 A1 | 9/2009 | Demarais et al. |
| 2009/0228003 A1 | 9/2009 | Sinelnikov |
| 2009/0248011 A1 | 10/2009 | Hlavka et al. |
| 2009/0299360 A1 | 12/2009 | Ormsby |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0033940 A1 | 2/2010 | Yamaguchi et al. |
| 2010/0049099 A1 | 2/2010 | Thapliyal et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1 | 7/2010 | Wu et al. |
| 2010/0168737 A1 | 7/2010 | Grunewald |
| 2010/0168739 A1 | 7/2010 | Wu et al. |
| 2010/0174282 A1 | 7/2010 | Demarais et al. |
| 2010/0179424 A1 | 7/2010 | Warnking et al. |
| 2010/0189974 A1* | 7/2010 | Ochi ..................... B32B 15/08 428/213 |
| 2010/0191112 A1 | 7/2010 | Demarais et al. |
| 2010/0198065 A1 | 8/2010 | Thapliyal et al. |
| 2010/0249859 A1 | 9/2010 | DiLorenzo |
| 2010/0291722 A1* | 11/2010 | Kim ........................ C23F 1/18 438/38 |
| 2011/0004184 A1 | 1/2011 | Proksch et al. |
| 2011/0054515 A1 | 3/2011 | Bridgeman et al. |
| 2011/0060324 A1 | 3/2011 | Wu et al. |
| 2011/0087096 A1 | 4/2011 | Behar |
| 2011/0087097 A1 | 4/2011 | Behar |
| 2011/0104060 A1 | 5/2011 | Seward |
| 2011/0112400 A1 | 5/2011 | Emery et al. |
| 2011/0118598 A1 | 5/2011 | Gertner |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0200171 A1 | 8/2011 | Beetel et al. |
| 2011/0208096 A1 | 8/2011 | Demarais et al. |
| 2011/0257523 A1 | 10/2011 | Hastings et al. |
| 2011/0257562 A1 | 10/2011 | Schaer |
| 2011/0257563 A1 | 10/2011 | Thapliyal et al. |
| 2011/0257564 A1 | 10/2011 | Demarais et al. |
| 2011/0301662 A1 | 12/2011 | Bar-Yoseph et al. |
| 2011/0319765 A1 | 12/2011 | Gertner et al. |
| 2012/0004656 A1 | 1/2012 | Jackson et al. |
| 2012/0065493 A1 | 3/2012 | Gertner |
| 2012/0065554 A1 | 3/2012 | Pikus |
| 2012/0071918 A1 | 3/2012 | Amin et al. |
| 2012/0078278 A1 | 3/2012 | Bales et al. |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0215106 A1 | 8/2012 | Sverdlik et al. |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0316439 A1 | 12/2012 | Behar |
| 2013/0012844 A1 | 1/2013 | Demarais et al. |
| 2013/0072928 A1 | 3/2013 | Schaer |
| 2013/0090650 A1 | 4/2013 | Jenson et al. |
| 2013/0103064 A1 | 4/2013 | Arenson et al. |
| 2013/0110012 A1 | 5/2013 | Gertner |
| 2013/0131668 A1 | 5/2013 | Schaer |
| 2013/0138018 A1 | 5/2013 | Gertner |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0218054 A1 | 8/2013 | Sverdlik et al. |
| 2013/0274658 A1 | 10/2013 | Steinke et al. |
| 2013/0282084 A1 | 10/2013 | Mathur et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0067029 A1 | 3/2014 | Schauer et al. |
| 2014/0074083 A1 | 3/2014 | Horn et al. |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0272110 A1 | 9/2014 | Taylor et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2015/0223877 A1 | 8/2015 | Behar et al. |
| 2015/0290427 A1 | 10/2015 | Warnking |
| 2015/0335919 A1 | 11/2015 | Behar et al. |
| 2016/0016016 A1 | 1/2016 | Taylor et al. |

FOREIGN PATENT DOCUMENTS

| | | |
|---|---|---|
| EP | 0 767 630 B1 | 4/1997 |
| EP | 0 838 980 | 4/1998 |

(56) References Cited

FOREIGN PATENT DOCUMENTS

| | | |
|---|---|---|
| EP | 1 100 375 B1 | 5/2001 |
| EP | 1 384 445 A1 | 1/2004 |
| EP | 1 647 305 B1 | 4/2006 |
| EP | 2 218 479 A2 | 8/2010 |
| EP | 2 359 764 A1 | 8/2011 |
| EP | 2 457 614 A1 | 5/2012 |
| EP | 2 460 486 B1 | 6/2012 |
| EP | 2 495 012 A1 | 9/2012 |
| EP | 2 521 593 B1 | 11/2012 |
| EP | 2 561 903 A1 | 2/2013 |
| EP | 2 561 905 A1 | 2/2013 |
| EP | 2 626 022 A2 | 8/2013 |
| EP | 2 632 373 | 9/2013 |
| EP | 2 662 041 A2 | 11/2013 |
| EP | 2 662 043 A2 | 11/2013 |
| JP | 05-068684 A | 3/1993 |
| JP | 40826437 * | 10/1996 |
| JP | 10-507229 A | 7/1998 |
| JP | 2000-054153 | 2/2000 |
| JP | 2001-111126 * | 4/2001 |
| JP | 2001-111126 A | 4/2001 |
| JP | 2005-526579 A | 9/2005 |
| JP | 2006-161116 A | 6/2006 |
| JP | 2008-515544 A1 | 5/2008 |
| JP | 2008-214669 * | 9/2008 |
| JP | 2010-503466 A1 | 2/2010 |
| JP | 2011-219828 A | 11/2011 |
| WO | WO-99/02096 A1 | 1/1999 |
| WO | WO-00/41881 A2 | 7/2000 |
| WO | WO-03/059437 A2 | 7/2003 |
| WO | WO-03/099382 A1 | 12/2003 |
| WO | WO-2004/091255 A1 | 10/2004 |
| WO | WO-2005/009218 A2 | 2/2005 |
| WO | WO-2006/041847 A1 | 4/2006 |
| WO | WO-2006/041881 A2 | 4/2006 |
| WO | WO-2006/060053 A2 | 6/2006 |
| WO | WO-2007/124458 A2 | 11/2007 |
| WO | WO-2007/135875 A1 | 11/2007 |
| WO | WO-2007/146834 A2 | 12/2007 |
| WO | WO-2008/003058 A2 | 1/2008 |
| WO | WO-2008/036479 A2 | 3/2008 |
| WO | WO-2008/052186 A2 | 5/2008 |
| WO | WO-2008/061152 A2 | 5/2008 |
| WO | WO-2008/151001 A2 | 12/2008 |
| WO | WO-2009/029261 | 3/2009 |
| WO | WO-2009/149315 | 12/2009 |
| WO | WO-2010/033940 A1 | 3/2010 |
| WO | WO-2010/067360 A2 | 6/2010 |
| WO | WO-2011/046880 A2 | 4/2011 |
| WO | WO-2011/053757 A1 | 5/2011 |
| WO | WO-2011/082279 A2 | 7/2011 |
| WO | WO-2011/088399 A1 | 7/2011 |
| WO | WO-2011/094367 A1 | 8/2011 |
| WO | WO-2011/139589 A2 | 11/2011 |
| WO | WO-2012/112165 | 8/2012 |

OTHER PUBLICATIONS

International Search Report & Written Opinion dated Feb. 16, 2015 in Int'l PCT Patent Appl Serial No. PCT/IB2014/001771.
International Search Report dated Feb. 9, 2014 in Int'l PCT Patent Appl Serial No. PCT/US2014/022796.
Extended EP Search Report dated Dec. 5, 2016 in EP Patent Application Serial No. 16183988.1.
Bhatt, et al., A Controlled Trial of Renal Denervation for Resistant Hypertension, N. Engl. J. Med., 370:1393-1401 (2014).
Bunch, Jared, et al., Mechanisms of Phrenic Nerve Injury During Radiofrequency Ablation at the Pulmonary Vein Orifice, Journal of Cardiovascular Electrophysiology, 16(12):1318-1325 (2005).
Campese, et al., Renal afferent denervation prevents hypertension in rats with chronic renal failure, Hypertension, 25:878-882 (1995).
Dibona, Renal nerves in compensatory renal response to contralateral renal denervation, Renal Physiology, 238 (1):F26-F30 (1980).
International Search Report & Written Opinion dated Jul. 9, 2014 in Int'l PCT Patent Application Serial No. PCT/US2014/22804.
International Search Report & Written Opinion dated Nov. 29, 2011 in International PCT Patent Appl No. PCT/US2011/025543.
Medtronic Announces U.S. Renal Denervation Pivotal Trial Fails to Meet Primary Efficacy Endpoint While Meeting Primary Safety Endpoint, Medtronic Press Release, Jan. 9, 2014.
Oliveira, et a., Renal Denervation Normalizes Pressure and Baroreceptor Reflex in High Renin Hypertension in Conscious Rats, Hypertension 19:17-21 (1992).
OnlineMathLearning.com, Volume Formula, "Volume of a Hollow Cylinder", Oct. 24, 2008.
Smithwick, R.H., Surgery in hypertension, Lancet, 2:65 (1948).
Smithwick, R.H., Surgical treatment of hypertension, Am J Med 4:744-759 (1948).
Wang, S., et al., Effects of Low Intensity Ultrasound on the Conduction Property of Neural Tissues, IEEE International Ultrasonics, Ferroelectrics, and Frequency Control, Joint 50th Anniversary Conference, 2004.

* cited by examiner

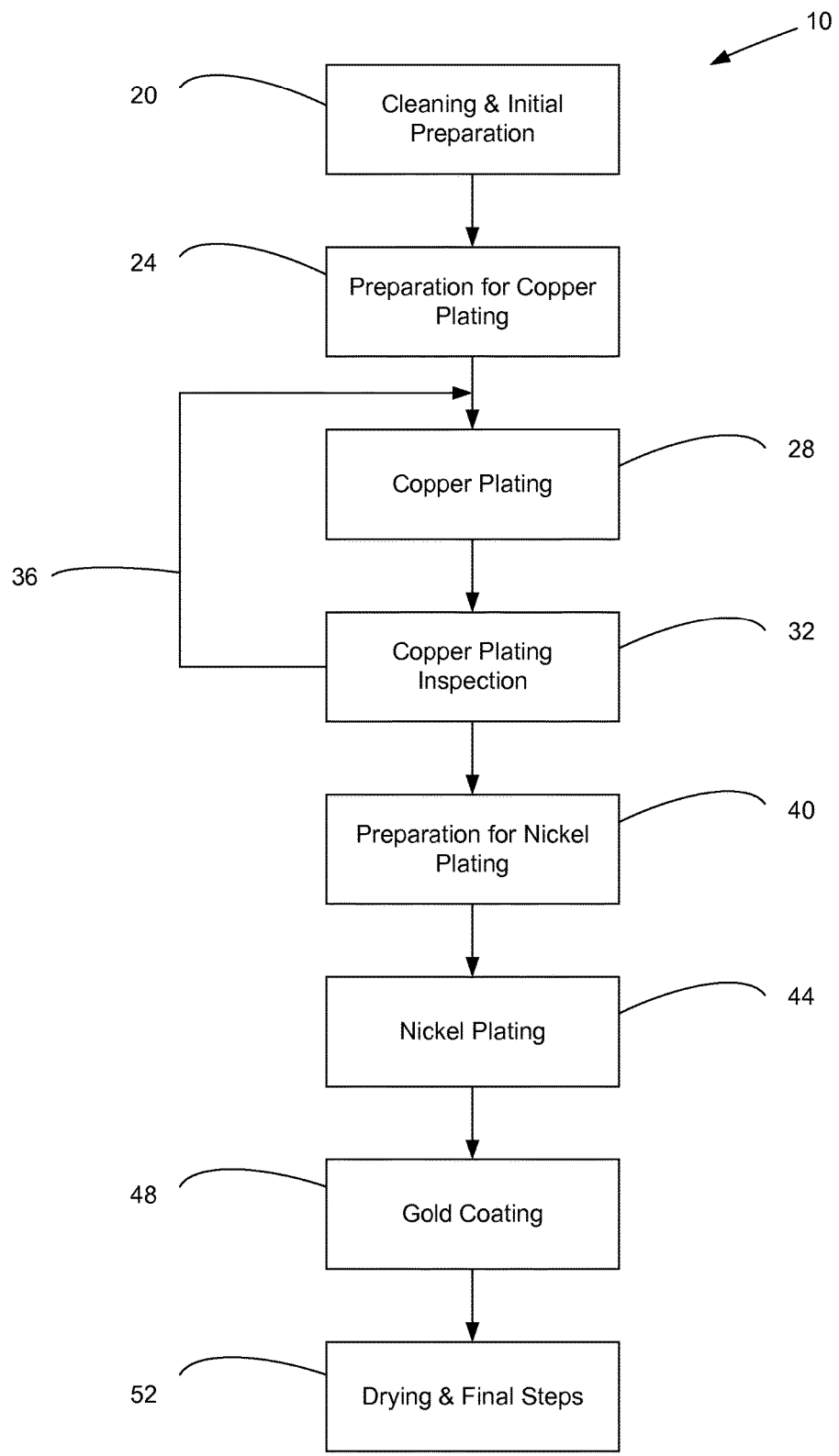

METHODS OF PLATING OR COATING ULTRASOUND TRANSDUCERS

CROSS-REFERENCE TO RELATED APPLICATIONS

This application claims the priority benefit under 35 U.S.C. § 119(e) of U.S. Provisional Application No. 61/784,164, filed Mar. 14, 2013, the entirety of which is hereby incorporated by reference herein.

BACKGROUND

Field

This application relates generally to ultrasound transducers, and more specifically, to methods of plating or otherwise coating ceramic tubes to produce the electrodes of the transducer.

Description of the Related Art

Ultrasound transducers can comprise a ceramic base material having inner and/or outer electrodes that are electrically energized to produce acoustic energy. Therefore, methods of positioning the electrodes onto the surfaces of an ultrasound transducer are disclosed herein.

SUMMARY

According to some embodiments, a method of depositing at least one electrode on a base member of an ultrasound transducer comprises cleaning a base member with a cleaning agent, wherein the base member comprises a ceramic material. The method further comprises at least partially etching a surface of the base member using a first etching agent (e.g., an acid), catalyzing the surface of the base member using a first catalyst (e.g., a solution comprising palladium), plating copper on the surface of the base member using an electroless plating process, inspecting the copper plated on the surface of the base member, at least partially etching a surface of the copper-plated surface using a second etching agent (e.g., an acid), catalyzing the copper-plated surface using a second catalyst (e.g., a solution comprising palladium), plating nickel on the copper-plated surface using an electroless plating process and depositing at least one layer of gold on the nickel-plated surface.

According to some embodiments, the cleaning agent comprises a degreaser, an alcohol and/or the like. In some embodiments, the first etching agent and the second etching agent comprises an acid (e.g., Citranox, H2SO4, etc.). In some embodiments, plating copper on the surface of the base member comprises placing the base member in a copper bath. In some embodiments, inspecting the copper plated on the surface of the base member comprises verifying a thickness of copper plated on the base member, verifying a uniformity of plating along the base member and/or any other aspect of the quality and extent of the copper plating. According to some embodiments, if the base member does not meet at least one threshold requirement of the inspection, the method further comprises re-plating copper on the surface of the base member using an electroless plating process.

According to some embodiments, the second catalyst comprises a sulfate anion-based solution. In some embodiments, plating nickel on the copper-plated surface comprises placing the ultrasound transducer in a bath comprising high-phosphorus nickel. In some embodiments, depositing at least one layer of gold on the nickel-plated surface comprises immersing a monolayer of gold along the nickel-plated surface.

According to some embodiments, a thickness of copper along the surface of the base member is approximately 10-20 microinches (e.g., 15 microinches, 10-12, 12-14, 14-16, 16-18, 18-20 microinches, etc.). In some embodiments, a thickness of nickel along the copper-coated surface is approximately 100-200 microinches (e.g., 150 microinches, 100-120, 120-140, 140-160, 160-180, 180-200 microinches, etc.). In some embodiments, a thickness of gold along the nickel-coated surface is approximately 0.1-10 microinches (e.g., 5 microinches, 0-1, 1-2, 2-3, 4-5 microinches, etc.).

According to some embodiments, the base member comprises cylindrical shape. In some embodiments, the copper, nickel and gold are deposited along exterior and interior surface of the base member. In one embodiment, the base member comprises a piezoceramic material (e.g., PZT). In some embodiments, at least one electrode is deposited on a plurality of base members using a batch procedure (e.g., using a wire rack, a barrel system, etc.). In some embodiments, the base member is cut from a larger bulk member (e.g., a long ceramic cylinder).

BRIEF DESCRIPTION OF THE DRAWINGS

FIG. 1 schematically illustrates a flowchart of depositing an electrode on a base member of an ultrasound transducer according to one embodiment.

DETAILED DESCRIPTION

In some embodiments, ultrasound transducers include a cylindrical shape comprising a base material. Such a base material can comprise a ceramic, such as for example, lead zirconate titanate (PZT), other piezoelectric ceramic materials and/or the like. In some embodiments, a long cylindrical tube of ceramic base material is cut and/or otherwise machined into smaller sections to make individual transducers having a desired length. After a base tube portion has been produced, one or more metal plating processes can be used to selectively deposit one or more electrodes thereon. As discussed herein, the electrodes can include one or more metals, alloys and/or other electrically conductive materials. One embodiment of a transducer plating method 10 is shown schematically in the flowchart of FIG. 1. In any of the embodiments disclosed herein, a plurality of the cylindrical tubes can be prepared and coated at the same time, e.g., in a batch system. For example, in some embodiments, a plurality of transducer tubes is positioned in a rack system (e.g., wire rack), a barrel system and/or the like. Accordingly, the multiple tubes can be simultaneously submerged, at least partially, into one or more baths or solutions during the preparation, plating and/or other manufacturing steps.

Cleaning and Initial Preparation

In some embodiments, machining oil, other oils, grease, natural coatings or layers and/or other materials are used to produce the individual tube lengths. Thus, it may be desirable or required to clean and otherwise prepare 20 the tubes before beginning the coating process. For example, in some embodiments, the process includes degreasing the tube using an ultrasonic degreaser, alcohol-based cleaner and/or any other cleaning product or agent. As noted above, the tubes can be submerged or otherwise placed within a bath (e.g., degreasing solution). After a particular time period of exposure to the degreaser or other cleaner (e.g., ~1 minute), the tubes can be removed and placed in a deionized water solution or bath (e.g., for ~1 minute) to remove excess degreaser and/or other cleaning solution.

Next, in one embodiment, the surface of the tube can be further cleaned using an acid cleaner and/or other etching material. For example, the tube can be placed in a Citranox® solution or other relatively weak acid solution for about 1 minute. This can help remove additional unwanted layers, coatings and/or materials from the exposed, exterior surfaces (e.g., inner and outer) of the tube. In some embodiments, such a weak acid cleaning step at least partially etches the outer surfaces of the tube. A water rinse (e.g., using deionized water) can be used to remove excess acid cleaner from the tube.

Preparation for Copper Plating

In some embodiments, the tubes are initially plated with copper. Certain preparatory steps 24 can be taken, in some embodiments, in advance of the copper plating process. For example, the tube can be placed in a strong acid solution, such as, e.g., a 10% solution of HBF4 and Acetate. In one embodiment, the tube is exposed to this solution for about 90 seconds. As a result of such an exposure, the tube's outer surfaces can be at least partially etched. This can help remove lead and/or other undesirable substances that may interfere with the subsequent copper plating steps. In some embodiments, care must be taken to prevent damage to the geometry of the tube. In other words, if an excessive amount of etching is performed, the cylindrical shape of the tube can be changed, thereby negatively impacting the acoustic energy profile of the transducer. For example, if the tube is not cylindrical within a particular tolerance level, the acoustic energy emitted by the transducer may be unevenly delivered in the radial direction (e.g., creating hot spots, spots of lower energy intensity, etc.).

Once the tube has been adequately etched, it can be rinsed to remove any excess etching solution or material. For example, in one embodiment, the tube can be subjected to one, two or more deionized water rinses. For example, in some embodiments, the tubes are subjected to two separate deionized water rinse cycles, each of which can last about 30 seconds.

In some embodiments, the transducer tube is then subjected to a clean copper dummy load solution, e.g., a 10% solution of HBF4 for about 1 minute. Such a step can help make the outer and inner surfaces of the tube more reactive for the subsequent copper plating step. In some embodiments, one or more sheets or other members comprising copper are positioned within a bath or solution into which the tube is placed. For example, in some embodiments, about ½ square foot of surface area of one or more copper-containing components (e.g., plates) are placed in the bath about 1 to 5 minutes prior to starting the actual copper plating procedure.

Following its exposure to copper dummy load solution, the transducer tube can be rinsed during a water rinse stage. In some embodiments, the tube can be rinsed, for example, using deionized water for about 30 seconds.

Copper Plating

With continued reference to FIG. 1, in some embodiments, following the copper plating preparation step, the transducer tube can proceed to a copper plating process 28. In one embodiment, the surfaces of the tube can be treated for the subsequent application of one or more plating catalysts. For example, the tube can be exposed to Enthone 432 for about 1 minute. In some arrangements, the Enthone or other preparatory solution is exposed to one or more rinsing steps. For example, the tube can go through two rinsing steps using deionized water, each of which can last about 20 seconds.

Next, in some embodiments, the surfaces of the transducer tube can be catalyzed, at least in part, with palladium. For example, the tube can be placed in a bath of Enthone 440 for about 3 minutes. In some embodiments, the palladium is a catalyst to assist in the subsequently plating of copper onto the tube surface. One or more other catalysts can be used, either in lieu of or in addition to palladium. Excess Enthone 432 and/or other palladium-containing solution can then be removed using a quick dip procedure.

Once the surfaces of a transducer tube have been prepared, it can be placed in a bath or other solution of Enthone 406 to allow the copper to plate onto the tube. For example, in some embodiments, the tubes are kept in such a bath for about 10 minutes. In some embodiments, such a plating process can result in a copper coating on the tube of about 10-20 microinches (e.g., 15 microinches).

Copper Plating Inspection

In some embodiments, if, after an inspection phase 32, it is determined that the plating of the copper is inadequate (e.g., insufficient plating thickness, non-uniform plating, etc.), the tube can be exposed to another copper plating cycle 28. Thus, as schematically illustrated by step 36 in FIG. 1, the need to begin the plating process from the beginning (e.g., step 20 or 24 in FIG. 1) can be eliminated. This type of short-circuiting step 36 in the process 10 can reduce manufacturing time, simplify the manufacturing protocol and provide one or more benefits and advantages. In some embodiments, the short-circuiting step 36 can be repeated up to about 4 times before a transduce tube is discarded.

Nickel Plating Preparation

If the copper plating is satisfactory, the tube can be subjected to subsequent nickel plating steps. In some embodiments, after the copper plating and inspection steps 28, 32, the tube can proceed to a nickel plating preparatory process 40. For example, the tube can be rinsed using a deionized water rinse for about 20 seconds before being exposed to an etching step. In some embodiments, the copper-plated tube can be at least partially etched in a 10% $H_2SO_4$ solution for about 30 seconds. The use of $H_2SO_4$ can provide a better match for the sulfate anion used in the previous copper plating steps, thereby facilitating the nickel plating process.

In some embodiments, once the copper-plated tube has been etched, it can be subjected to a palladium catalyst solution (e.g., TechniCatalyst AT 4000). For example, the tube can be placed in a palladium catalyst solution for about 2 minutes. In some embodiments, the palladium catalyst solution comprises a sulfate ion activator. In some embodiments, the palladium catalyst solution does not comprise a chloride ion activator. After exposure to the palladium catalyst, the copper dummy load can be terminated and the tube can be rinsed to remove any excess palladium catalyst solution (e.g., using deionized using a quick dip procedure).

Nickel Plating

In some embodiments, the transducer tube can then proceed to the nickel plating process 44. For example, the tube can be placed in a nickel solution for approximately 15 minutes. In some embodiments, the nickel solution comprises a high-phosphorus nickel solution (e.g., NICHEM 5100). As a result of the exposure to such a nickel solution, in some embodiments, about 100-200 microinches (e.g., 150 microinches) of nickel can be electroplated onto the outside surface of the transducer tube (e.g., over the electroplated copper layer). After the nickel has been adequately plated on the outside surfaces of the transducer tube, excess nickel solution can be removed by rinsing the tube with deionized water for about 20 seconds.

Gold Immersion

In some embodiments, a layer of gold can be positioned 48 along the outside of the copper and nickel layers that have been plated on the transducer tube. For example, the gold can be immersed as a monolayer onto the outside of the tube. In other embodiments, more than one layer (e.g., 2, 3, more than 3, etc.) layers of gold are used, as desired or required. In some embodiments, the tube is subjected to an immersion of gold (e.g., OMG Fidelity 9027+potassium gold) for about 2 minutes. The use of such an immersion layer can eliminate or reduce the likelihood of complications resulting from electrolytic plating of gold onto the surfaces of the cylinder, especially within the interior surfaces of relatively small cylinders. Therefore, in some embodiments, the gold is placed onto the transducer tube without using an electrolytic process. In some embodiments, the thickness of the gold monolayer deposited on the tube (e.g., along the outside of the copper and nickel layers) is about 2-10 microinches (e.g., 5 microinches). Following the gold immersion process, any excess gold can be removed from the outside of the tube using deionized water rinse (e.g., for about 20 seconds).

Drying and Completion

According to some embodiments, after the desired layers of copper, nickel, gold and/or any other material have been placed along the outside of the transducer tube, the tube can undergo one or more finishing steps 52. For example, an alcohol rinse (comprising, e.g., isopropyl alcohol) can be used to remove any excess water and to facilitate drying of the outer surfaces of the tube. Finally, in some embodiments, the tube can be placed in an oven or other thermal environment to remove the alcohol and dry the tube.

A transducer tube plated and/or otherwise coated in accordance with the various embodiments disclosed herein can include three different metals, such as, for example, a copper base layer, a nickel intermediate layer and a gold outer layer. In some embodiments, the thickness of the various metals placed on the tube can be about 150-200 microinches. For example, in one embodiment, a transducer can include a base layer of copper, an intermediate layer of nickel and an outer layer of gold having thicknesses of about 15 microinches, 150 microinches and 5 microinches, respectively. IN other embodiments, the thickness of one or more layers can vary, as desired or required.

Additional details regarding possible ultrasonic transducer designs and embodiments (e.g., both structurally and operationally) are provided in U.S. patent application Ser. No. 11/267,123, filed on Jul. 13, 2001 and published as U.S. Publ. No. 2002/0068885 on Jun. 6, 2002 and issued as U.S. Pat. No. 7,540,846 on Jun. 2, 2009; U.S. patent application Ser. No. 09/905,227, filed Jul. 13, 2001 and issued as U.S. Pat. No. 6,635,054 on Oct. 21, 2003; U.S. patent application Ser. No. 09/904,620, filed on Jul. 13, 2001 and issued as U.S. Pat. No. 6,763,722 on Jul. 20, 2004; U.S. patent application Ser. No. 10/783,310, filed Feb. 20, 2004 and issued as U.S. Pat. No. 7,837,676 on Nov. 23, 2010; U.S. patent application Ser. No. 12/227,508, filed on Feb. 3, 2010 and published as U.S. Publ. No. 2010/0130892 on May 27, 2010; U.S. patent application Ser. No. 10/611,838, filed on Jun. 30, 2003 and published as U.S. Publ. No. 2004/0082859 on Apr. 29, 2004 Now abandoned; and PCT Appl. No. PCT/US2011/025543, filed on Feb. 18, 2011 and published as PCT Publ. No. WO 2012/112165 on Aug. 23, 2012. The entireties of all the foregoing applications is hereby incorporated by reference herein and made a part of the present application.

The features and attributes of the specific embodiments disclosed herein may be combined in different ways to form additional embodiments, all of which fall within the scope of the present disclosure. Although the concepts presented herein have been disclosed in the context of certain embodiments and examples, the present application extends beyond the specifically disclosed embodiments to other alternative embodiments and/or uses of the concepts disclosed herein and obvious modifications and equivalents thereof. The disclosure herein of any particular feature, aspect, method, property, characteristic, quality, attribute, element, or the like in connection with an embodiment can be used in all other embodiments set forth herein. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." For all of the embodiments described herein the steps of the methods need not be performed sequentially. Thus, it is intended that the scope of the concepts disclosed herein should not be limited by the particular disclosed embodiments described above.

What is claimed is:

1. A method of depositing at least one electrode on a base member of an ultrasound transducer, the method comprising:
    cleaning a base member with a cleaning agent, wherein the base member comprises ceramic;
    at least partially etching a surface of the base member using a first etching agent comprising a solution of tetrafluoroboric acid and acetate;
    catalyzing the surface of the base member using a first catalyst;
    plating copper on the surface of the base member using an electroless plating process such that the copper is adjacently deposited onto the base member;
    inspecting the copper plated on the surface of the base member;
    at least partially etching a surface of the copper-plated surface using a second etching agent;
    catalyzing the copper-plated surface using a second catalyst;
    plating nickel on the copper-plated surface using an electroless plating process; and
    depositing at least one layer of gold on the nickel-plated surface.

2. The method of claim 1, wherein the cleaning agent comprises at least one of a degreaser and an alcohol.

3. The method of claim 1, wherein the second etching agent comprises an acid.

4. The method of claim 1, wherein at least one of the first catalyst and the second catalyst comprises palladium.

5. The method of claim 1, wherein plating copper on the surface of the base member comprises placing the base member in a copper bath.

6. The method of claim 1, wherein the second catalyst comprises a sulfate anion-based solution.

7. The method of claim 1, wherein plating nickel on the copper-plated surface comprises placing the ultrasound transducer in a bath comprising high-phosphorus nickel.

8. The method of claim 1, wherein depositing at least one layer of gold on the nickel-plated surface comprises immersing a monolayer of gold along the nickel-plated surface.

9. The method of claim 1, wherein a thickness of copper along the surface of the base member is approximately 15 microinches.

10. The method of claim 1, wherein a thickness of nickel along the copper-coated surface is approximately 150 microinches.

11. The method of claim 1, wherein a thickness of gold along the nickel-coated surface is approximately 5 microinches.

12. The method of claim 1, wherein the base member is cut from a larger bulk member.

13. The method of claim 1, wherein inspecting the copper plated on the surface of the base member comprises at least one of verifying a thickness of copper plated on the base member and verifying a uniformity of plating along the base member.

14. The method of claim 13, wherein, if the base member does not meet at least one threshold requirement of the inspection, the method further comprises re-plating copper on the surface of the base member using an electroless plating process.

15. The method of claim 1, wherein the base member comprises cylindrical shape.

16. The method of claim 15, wherein the copper, nickel and gold are deposited along exterior and interior surface of the base member.

17. The method of claim 1, wherein at least one electrode is deposited on a plurality of base members using a batch procedure.

18. The method of claim 17, wherein the plurality of base members is positioned on a wire rack.

19. The method of claim 17, wherein the plurality of base members is positioned in a barrel system.

* * * * *